United States Patent [19]
Bradley et al.

[11] Patent Number: 5,955,459
[45] Date of Patent: Sep. 21, 1999

[54] FATTY ACID-ANTIPSYCHOTIC COMPOSITIONS AND USES THEREOF

[75] Inventors: Matthews O. Bradley, Laytonsville, Md.; Victor E. Shashoua, Belmont, Mass.; Charles S. Swindell, Merion; Nigel L. Webb, Bryn Mawr, both of Pa.

[73] Assignee: Neuromedica, Inc., Conshohocken, Pa.

[21] Appl. No.: 08/979,312

[22] Filed: Nov. 26, 1997

[51] Int. Cl.$^6$ .................................................. A61R 31/395
[52] U.S. Cl. ........................ 514/220; 514/234; 514/255; 514/321
[58] Field of Search ..................... 514/220, 234, 514/255, 321

[56] References Cited

U.S. PATENT DOCUMENTS

| | | | |
|---|---|---|---|
| 3,539,573 | 11/1970 | Schmutz et al. | 260/268 |
| 4,097,597 | 6/1978 | Horrom et al. | 514/220 |
| 4,558,049 | 12/1985 | Lazzari et al. | 514/234 |
| 4,692,441 | 9/1987 | Alexander et al. | 514/194 |
| 4,939,174 | 7/1990 | Shashoua | 514/549 |
| 5,112,863 | 5/1992 | Hashimoto et al. | 514/534 |
| 5,214,062 | 5/1993 | Mark et al. | 514/369 |
| 5,223,263 | 6/1993 | Hostetler et al. | 424/450 |
| 5,308,832 | 5/1994 | Garleb et al. | 514/2 |
| 5,411,947 | 5/1995 | Hostetler et al. | 514/43 |
| 5,466,841 | 11/1995 | Horrobin et al. | 554/79 |
| 5,516,800 | 5/1996 | Horrobin | 514/560 |
| 5,532,374 | 7/1996 | Saji et al. | 544/368 |
| 5,604,198 | 2/1997 | Poduslo et al. | 514/6 |
| 5,604,216 | 2/1997 | Horrobin | 514/182 |
| 5,646,180 | 7/1997 | Chaturvedi | 514/471 |
| 5,654,290 | 8/1997 | Bayon et al. | 514/77 |
| 5,750,572 | 5/1998 | Bruzzese | 514/560 |
| 5,795,909 | 8/1998 | Shashoua et al. | 514/449 |
| 5,827,819 | 10/1998 | Yatvin et al. | 514/2 |

FOREIGN PATENT DOCUMENTS

| | | |
|---|---|---|
| 0599 576 A1 | 1/1994 | European Pat. Off. . |
| 693498 | 1/1996 | European Pat. Off. . |
| 06 072868 | 3/1994 | Japan . |
| 6072868 | 3/1994 | Japan . |
| 7082146 | 3/1996 | Japan . |
| 8151334 | 6/1996 | Japan . |
| 9030963 | 2/1997 | Japan . |
| WO 98/17325 | 4/1998 | WIPO . |

OTHER PUBLICATIONS

Schabitz WR, et al., "The Effects of Prolonged Treatment With Citicoline in Temporary Experimental Focal Ischemia", *J Neurol Sci*, 1996, 138(1–2):21–25. (Abstract).

D'Orlando KJ, et al., "Citicoline (CDP–Choline): Mechanisms of Action and Effects in Ischemic Brain Injury", *Neurol Res*, 1995, 17(4): 281–284. Review.

Nishio K, et al., "Novel Water–Soluble Derivatives of Docosahexaenoic Acid Increase Diacyl–Glycerol Production Mediated by Phosphatidylcholine–Specific Phospholipase C", *Proc Soc Exp Biol Med*, 1993, 203(2): 200–208.

Marder, Stephen R., J. Clin. Psychiatry (suppl 3) 57: 9–13 (1996).

Copy of Office Action in related case U.S. Serial No. 08/978,541.

*Primary Examiner*—James H. Reamer
*Attorney, Agent, or Firm*—Wolf, Greenfield & Sacks, P.C.

[57] ABSTRACT

The invention provides compositions that include conjugates of a fatty acid molecule, preferably cis-docosahexaenoic acid, and antipsychotic agents. The conjugates are usefull in treating psychotic conditions such as schizophrenia.

32 Claims, 5 Drawing Sheets

FATTY ACID-ANTIPSYCHOTIC COMPOSITIONS AND USES THEREOF

RELATED APPLICATION

This application claims priority under 35 U.S.C. §120 from U.S. patent application Ser. Nos. 08/651,428, and 08/651,312, both filed May 22, 1996 the entire disclosures of which are incorporated herein by reference.

BACKGROUND OF THE INVENTION

Psychotic conditions such as schizophrenia and related disorders (e.g. schizoaffective disorder), are complex and heterogeneous diseases of uncertain etiology that afflict approximately 1 to 2% of all populations worldwide. Schizophrenia is characterized as having both "positive symptoms" (hallucinations, delusions, and conceptual disorganization) and "negative symptoms" (apathy, social withdrawal, affect, and poverty of speech). Abnormal activity of the neurotransmitter dopamine is a hallmark of schizophrenia. Dopaminergic activity is reduced in the mesocortical system (resulting in negative symptoms) and is enhanced in the mesolimbic system (resulting in positive or psychotic symptoms). Several other neurotransmitters are involved, including serotonin, glutamate, and GABA.

For many years, schizophrenia was treated with classical antipsychotic drugs, the neuroleptics, that block central dopamine receptors. The neuroleptics are effective for treating the positive symptoms of schizophrenia, but have little or no effect on the negative symptoms. The ability of these drugs to antagonize dopamine receptors correlates with antipsychotic efficacy. Neuroleptic drugs include phenothiazines including aliphatics (e.g., chlorpromazine), piperidines (e.g., thioridazine), and piperazines (e.g., fluphenazine); butyrophenones (e.g., haloperidol); thioxanthenes (e.g., flupenthixol); oxoindoles (e.g., molindone); dibenzoxazepines (e.g., loxapine) and diphenylpiperidines (e.g., pimozide).

Unfortunately, neuroleptics-resistant negative symptoms account for most of the social and vocational disability caused by schizophrenia. Further, neuroleptics cause extrapyramidal symptoms, including rigidity, tremor, bradykinesia (slow movement), and bradyphrenia (slow thought), as well as tardive dyskinesias and dystonias.

The atypical antipsychotics are a different class of antipsychotic drugs which have a different receptor binding profile and effectiveness against the symptoms of schizophrenia. Atypical antipsychotics bind central serotonin2 (5-HT2) receptors in addition to D2 dopamine receptors. Unlike the neuroleptics, they improve negative as well as positive symptoms. They cause minimal extrapyramidal symptoms and rarely cause tardive dyskinesias, akathisia, or acute dystonic reactions.

The first atypical antipsychotic drug approved for the treatment of schizophrenia was clozapine. Clozapine binds D2 dopamine receptor weakly, but has a strong affinity for the 5-HT2A receptor. Clozapine also antagonizes adrenergic, cholinergic, and histaminergic receptors. Clozapine is effective for the treatment of schizophrenia, especially for subjects who do not respond to traditional neuroleptic therapy. Clozapine has been found to be superior to neuroleptics for improving psychotic symptoms, and generally is better tolerated.

The side effects of clozapine, however, present problems for safety and patient compliance. The side effects include sedation, orthostatic hypotension, hypersalivation, lowered seizure threshold and, in particular, agranulocytosis. The incidence of agranulocytosis in patients taking clozapine is about 1–2%. Agranulocytosis is a serious condition characterized by a precipitous drop in the white blood cell count; the seriousness of the condition mandates that white blood cell counts be measured each week for patients taking clozapine. Another patient compliance issue is the relatively short half life of clozapine in vivo, which necessitates multiple doses each day to maintain therapeutic effectiveness.

Fatty acids previously have been conjugated with drugs to help the drugs as conjugates cross the blood brain barrier. For example, DHA (docosahexaenoic acid) is a 22 carbon naturally-occurring, unbranched fatty acid that previously has been shown to be unusually effective in crossing the blood brain barrier. When DHA is conjugated to a drug, the entire drug-DHA conjugate is transported across the blood brain barrier and into the brain. DHA is attached via the acid group to hydrophilic drugs and renders these drugs more hydrophobic (lipophilic). DHA is an important constituent of the brain and recently has been approved as an additive to infant formula. It is present in the milk of lactating women. The mechanism of action by which DHA helps drugs conjugated to it cross the blood brain barrier is unknown.

Another example of the conjugation of fatty acids to a drug is the attachment of pipotiazine, an antipsychotic, to stearic acid, palnitic acid, enanthic acid, undecylenic acid or 2,2-dimethyl-palmitic acid. Pipotiazine is a drug that acts within the central nervous system. The purpose of conjugating pipotiazine to the fatty acids was to create an oily solution of the drug as a liquid implant for slow release of the drug when injected intramuscularly. The release of the drug appeared to depend on the particular fatty acid selected, and the drug was tested for its activity in the central nervous system.

Lipidic molecules, including the fatty acids, also have been conjugated with drugs to render the conjugates more lipophilic than the drug. In general, increased lipophilicity has been suggested as a mechanism for enhancing intestinal uptake of drugs into the lymphatic system, thereby enhancing the entry of the conjugate into the brain and also thereby avoiding first-pass metabolism of the conjugate in the liver. The type of lipidic molecules employed have included phospholipids, non-naturally occurring branched and unbranched fatty acids, and naturally occurring branched and unbranched fatty acids ranging from as few as 4 carbon atoms to more than 30 carbon atoms. In one instance, enhanced receptor binding activity was observed (for an adenosine receptor agonist), and it was postulated that the pendant lipid molecule interacted with the phospholipid membrane to act as a distal anchor for the receptor ligand in the membrane microenvironment of the receptor. This increase in potency, however, was not observed when the same lipid derivatives of adenosine receptor antagonists were used, and generalizations thus were not made possible by those studies.

SUMMARY OF THE INVENTION

It has now been discovered that covalent conjugates of a fatty acid with clozapine have the unexpected property of extended therapeutic effectiveness. This unexpected property of the conjugate permits administration of lower doses of drug (as part of the covalent conjugate) to yield an antipsychotic therapeutic effect, thereby reducing the chances of serious side effects such as agranulocytosis. The unexpected property of the conjugate also permits less frequent dosing to maintain an antipsychotic therapeutic effect relative to unconjugated clozapine.

According to one aspect of the invention, a composition of matter is provided. The composition of matter is a covalent conjugate of an antipsychotic agent and a fatty acid having 12–26 carbons. Preferably the fatty acid in an unbranched common naturally occurring fatty acid. More preferably, the fatty acid has between 14 and 22 carbons.

Unbranched common naturally occurring fatty acids include C12:0 (lauric acid), C14:0 (myristic acid), C16:0 (palmitic acid), C16:1 (paalmitoleic acid), C16:2, C18:0 (stearic acid), C18:1 (oleic acid), C18:1-7 (vaccenic), C18:2-6 (linoleic acid), C18:3-3 (α-linolenic acid), C18:3-5 (eleostearic), C18:3-6 (β-linolenic acid), C18:4-3, C20:1 (gondoic acid), C20:2-6, C20:3-6 (dihomo-y-linolenic acid), C20:4-3, C20:4-6 (arachidonic acid), C20:5-3 (eicosapentaenoic acid), C22:1 (docosenoic acid), C22:4–6 (docosatetraenoic acid), C22:5-6 (docosapentaenoic acid), C22:5-3 (docosapentaenoic), C22:6-3 (docosahexaenoic acid) and C24:1-9 (nervonic). Highly preferred unbranched, naturally occurring fatty acids are those with between 14 and 22 carbon atoms. The most preferred fatty acid is docosahexaenoic acid.

Antipsychotic agents include:Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmnitate; Piquindone Hydrochloride; Prochlorperazine Edisylate; Prochlorperazine Maleate; Promazine Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

In certain preferred embodiments, involving compositions of matter, the conjugate of the fatty acid and the antipsychotic agent is selected from the foregoing agents, except that phenothiazines, butyrophenones and thioxanthenes are excluded.

The most preferred fatty acid is docosahexaenoic acid. The most preferred covalent conjugate is:

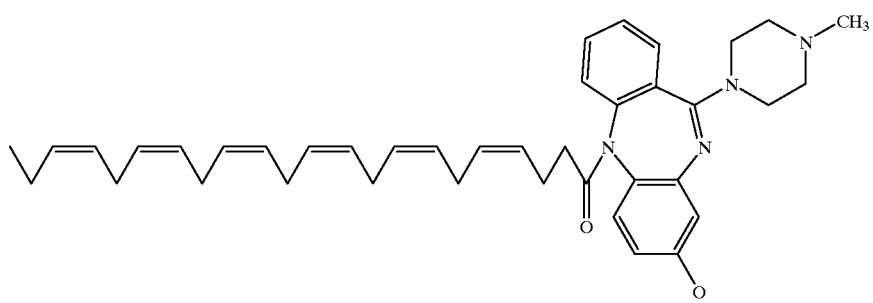

According to another aspect of the invention, a pharmaceutical composition is provided. The pharmaceutical composition includes a pharmaceutically acceptable carrier and a covalent conjugate of an antipsychotic agent and a fatty acid having 12–26 carbons. The covalent conjugate is present in the pharmaceutical composition in an amount effective for treating a psychotic condition. The preferred fatty acids, bonds, antipsychotic agents and covalent conjugates are as described above.

The pharmaceutical composition also may comprise an antipsychotic agent other than the covalent conjugate. Suitable such antipsychotic agents are selected from the group consisting of Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride;

Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

According to another aspect of the invention, a kit is provided. The kit comprises a package which houses a container containing the covalent conjugate as described above. The package also houses instructions for administering the covalent conjugate to a subject having a psychotic condition.

According to another aspect of the invention, a second kit is provided. The kit comprises a package which houses a first container containing the covalent conjugate described above and it further houses a second container containing an antipsychotic agent other than the covalent conjugate.

In the kits of the invention, the preferred fatty acids, bonds, antipsychotic agents and conjugates are as described above.

According to another aspect of the invention, a method is provided for treating a psychotic condition. The method involves administering to a subject in need of such treatment a covalent conjugate of an antipsychotic agent and a fatty acid having 12–26 carbons, in an amount effective to treat the psychotic condition. The preferred fatty acids, bonds, antipsychotic agents and conjugates are as described above. Likewise, cocktails as described above may be administered.

According to another aspect of the invention, a method is provided for achieving in a subject a therapeutic effect longer than the effect achieved if an equimolar amount of antipsychotic agents were administered. The method involves administering to a subject in need of such treatment a covalent conjugate of the antipsychotic agent and a fatty acid in an amount effective to achieve said therapeutic effect. The preferred fatty acids, bonds, antipsychotic agents and covalent conjugates are as described above.

According to still another aspect of the invention, a method is provided for decreasing the number of daily doses required to achieve in a subject a therapeutic effect equivalent to that achieved if an equimolar amount of antipsychotic agent were administered to the subject. The method involves administering to a subject in need of such treatment a covalent conjugate of antipsychotic agents and a fatty acid in an amount effective to achieve said therapeutic effect. Preferably, the covalent conjugate is administered not more than one time per day. The preferred fatty acids, bonds, antipsychotic agents and covalent conjugates are as described above.

These and other aspects of the invention are described below.

DETAILED DESCRIPTION OF THE INVENTION

Figure 1:
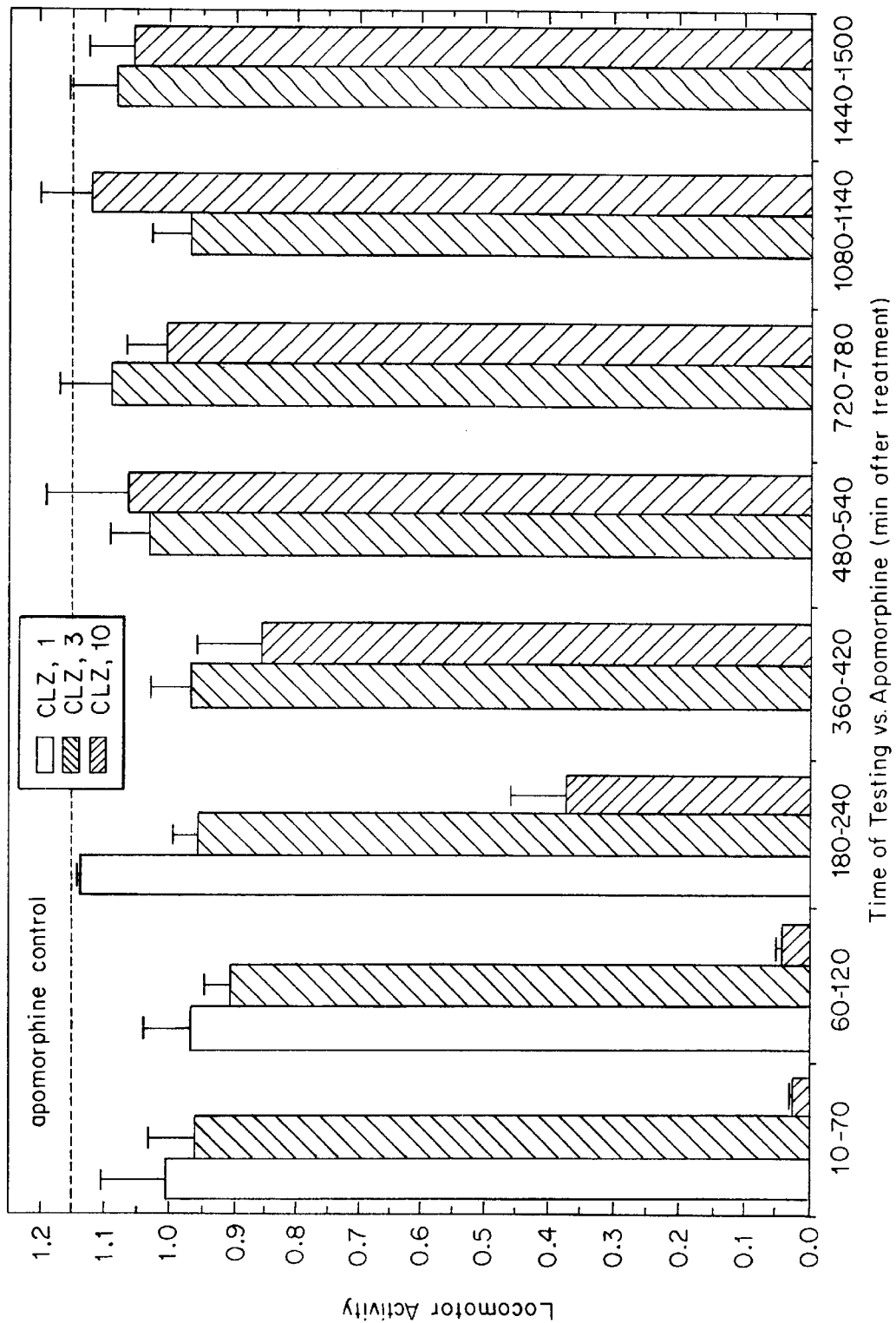
FIG. 1 is a graph which shows the dose response over time of clozapine against locomotor behavioral arousal induced by apomorphine. Clozapine 1, 3, 10 refer to doses of clozapine at 1, 3 and 10 mg/kg, respectively, administered i.p.

The invention involves the discovery that the extended therapeutic effectiveness can be achieved if conjugates of antipsychotic agents and fatty acids are administered rather than unconjugated antipsychotic agents.

Clozapine is one of the class of "atypical" antipsychotics, having the following structure:

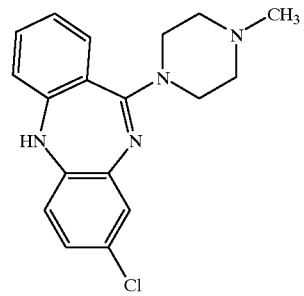

cis-docosahexaenoic acid (DHA) is a naturally occurring fatty acid. It is an unbranched chain fatty acid with six double bonds, all cis. Its structure is as follows:

DHA can be isolated, for example, from fish oil or can be chemically synthesized. These methods, however, can generate trans isomers, which are difficult and expensive to separate and which may present safety problems in humans. The preferred method of production is biological synthesis to produce the all cis isomer. The preferred source of DHA is from Martek Biosciences Corporation of Columbia, Maryland. Martek has a patented system for manufacturing DHA using microalgae which synthesize only a single isomer of DHA, the all cis isomer. Martek's patents include U.S. Pat. Nos. 5,374,657, 5,492,938, 5,407,957 and 5,397,591.

DHA also is present in the milk of lactating women, and Martek's licensee has obtained approval in Europe of DHA as a nutritional supplement for infant formula.

It is known that DHA can be unstable in the presence of oxygen. To stabilize DHA and its conjugates it is important to add anti-oxidants to the material after it is synthesized. One method of stabilization is to make-up the newly synthesized material in the following solution: 100 g neat DHA-clozapine plus 100 g of vehicle (100 ml propylene glycol, 70 mg alpha-tocopherol, 5 mg dialaurylthiodipropionic acid, 50 mg ascorbic acid) prepared and held under argon in amber, sealed vials and stored at four degrees centigrade. The following anti-oxidants may also be employed: ascorbic acid, ascorbyl palmitate, dilauryl ascorbate, hydroquinone, butyated hydroxyanisole, sodium meta bisulfite, t-β carotene and α-tocopherol. A heavy metal chelator such as ethylenediamine tetra-acetic acid (EDTA) may also be used.

In one aspect of the invention, cocktails of the clozapine-fatty acid conjugate and another antipsychotic agent can be prepared for administration to subjects having a need for such treatment. One of ordinary skill in the art is familiar with a variety of antipsychotic agents which are used in the medical arts to treat psychoses such as schizophrenia. Antipsychotic agents include Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

The compounds of the invention, when used in alone or in cocktails, are administered in therapeutically effective amounts. A therapeutically effective amount will be determined by the parameters discussed below; but, in any event, is that amount which establishes a level of the drug(s) effective for treating a psychotic disorder, including schizophrenia.

When administered, the formulations of the invention are applied in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa.

The invention is used in connection with treating subjects having, suspected of having, developing or suspected of developing a psychotic condition such as schizophrenia, or animals having or animals exhibiting symptoms characteristic of schizophrenia.

The conjugates of the invention, when used in alone or in cocktails, are administered in effective amounts. An effective amount means that amount alone or with multiple doses, necessary to delay the onset of, inhibit completely or lessen the progression of or halt altogether the onset or progression of the psychotic condition such as schizophrenia. In general, an effective amount will be that amount necessary to inhibit either negative or positive symptoms of the psychotic condition, and preferably both negative and positive symptoms of the psychotic condition such as schizophrenia. The inhibition of the negative and/or positive symptoms of schizophrenia can be monitored by standard psychiatric evaluation of the subject over time. In addition, other physiological methods for monitoring the changes in brain function which accompany symptoms of schizophrenia also can be employed to monitor the inhibition of the symptoms. For example, the state of advancement of schizophrenia can be assessed using magnetic resonance imaging (MRI) (see, e.g., DeLisi et al., (*Psychiatry Res*. 74(3):129–140, 1997) or positron emission tomography (PET) (see, e.g., Sabri et al., *Lancet* 349:1735–1739, 1997; Andreasen et al., Lancet 349:1730–1734, 1997). When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that IV doses in the same range will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day also are contemplated to achieve appropriate systemic levels of compounds.

The preferred dose is believed to be at least ½, more preferably ¼ and even more preferably ⅙ or less than the dose required to achieve the same therapeutic effect when an equimolar amount of antipsychotic agent is administered but nonconjugated to a fatty acid. Clozapine typically is administered in doses of 50–200 mg, 2–3 times per day.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, or infusion. Oral routes are preferred, although administration by injection may be practical.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

EXAMPLE

A) Synthesis of DHA-clozapine:

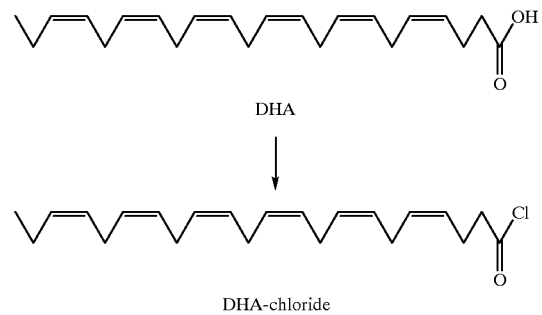

Preparation of DHA-chloride:

To a solution of DHA (2.0 g, 6.08 mmol) in $CH_2Cl_2$ (8 ml) was added thionylchloride (2.22 ml, 30.4 mmol), at 0° C. under an Argon atmosphere and the reaction mixture was stirred at room temperature for 14 h. Excess thionylchloride was removed by co-evaporation with dry benzene (6 ml) under reduced pressure. The resulting acid chloride was dried in high vacuum and subsequently used as such for the following reaction without purification.

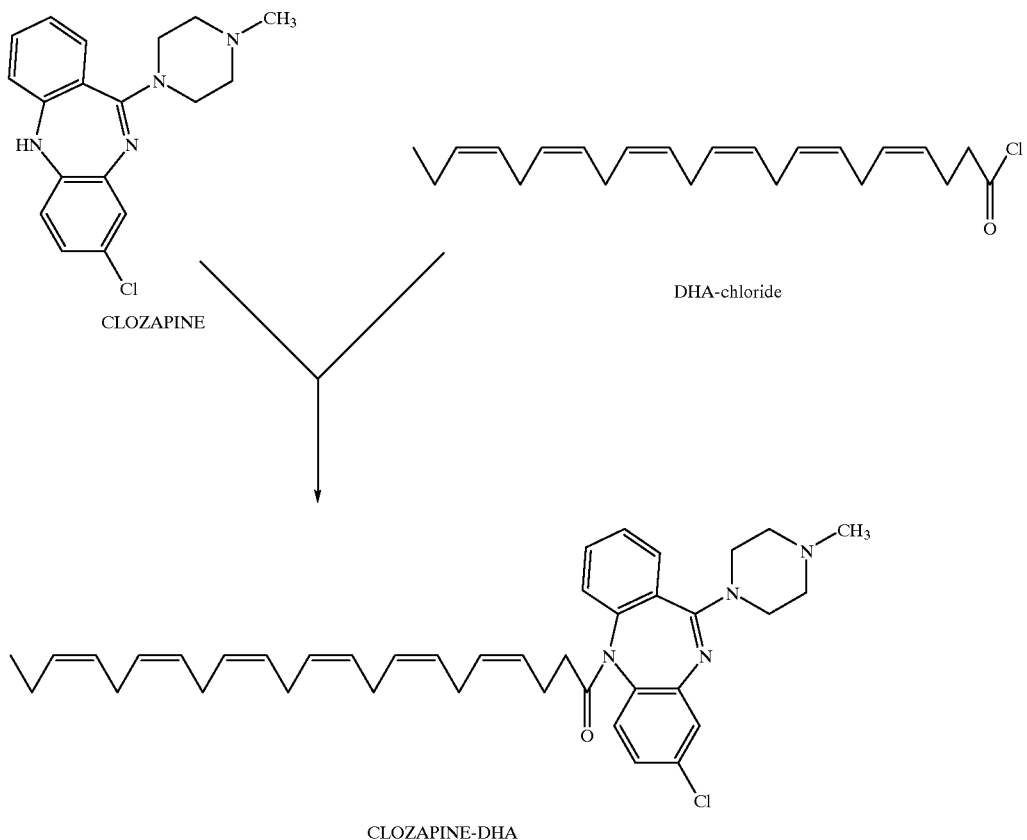

Preparation of Clozapine-DHA analog:

To a solution of clozapine (950 mg, 2.90 mmol) in dry toluene (30 ml) was added dry pyridine (235 μl, 2.90 mmol) followed by DHA-chloride (1.25 ml, 3.98 mmol) under an Argon atmosphere at room temperature. The reaction mixture was refluxed for 3 h, cooled to room temperature, and stirred with 10% aq. $Na_2CO_3$ solution (5 ml) for about 20 min. The reaction mixture was washed with water (3×20 ml), the combined aqueous phase was extracted once with ether (20 ml), the organic phase was dried ($Na_2SO_4$) and concentrated under reduced pressure. The residue was purified by chromatography on florisil with 98:2 $CHCl_3$-methanol as eluent to yield the clozapine-DHA analog as an orange red viscous liquid (1.65 g, 89%).

NMR analysis of the product was as follows:

$^1$H NMR (300 MMz, $CDCl_3$): δ0.97 (t, J=7.6 Hz, 3 H), 2.07 (apparent quintet, J=7.4 Hz, 2 H), 2.15–2.29 (m, 8 H), 2.29 (s, 3 H), 2.73–2.68 (m, 10 H), 3.48–3.90 (m, 4 H), 5.25–5.44 (m, 12 H), 6.96 (dd, J=8.4, 2.4 Hz, 1 H), 7.12 (d, J=8.4 Hz, 1 H), 7.36–7.50 (m, 3 H), 7.25–7.55 (m, 1 H).

$^3$C NMR (75 MHz, $CDCl_3$): δ14.22, 20.50 (2C), 22.82, 25.48, 25.49 (2C), 25.578 (4C), 33.44, 45.91, 54.66, 123.19, 126.10, 126.65, 126.97, 127.63, 127.81, 127.83 (2C), 128.07, 128.09, 128.15 (2C), 128.21 (2C), 128.51 (2C), 129.07 (2C), 131.97, 132.01, 133.37, 133.94, 144.72, 146.13, 160.29 and 172.98.

B) Methods of Use:
Experimental Procedures
  Animals: rats.
  Rats/group: nine.
  Route of administration: i.p.

Clozapine and DHA-clozapine were made-up to a 50% w/w solution in propylene glycol. This solution was injected directly into the peritoneum at the appropriate dose.

Physiological Measurements:

A standard animal model of schizophrenia symptoms (apomorphine increased hyper-locomotion) was used to assess the activity of the DHA-clozapine conjugate. To start the experiment, 1.0 mg/kg of R(−)apomorphine was injected into the peritoneum of each rat, which caused the locomotor activity of the rats to increase. The DHA-clozapine conjugate was then administered i.p., and the drug's effect on apomorphine increased hyper-locomotion was measured electronically in a computerized activity monitoring system.

Figure 2:
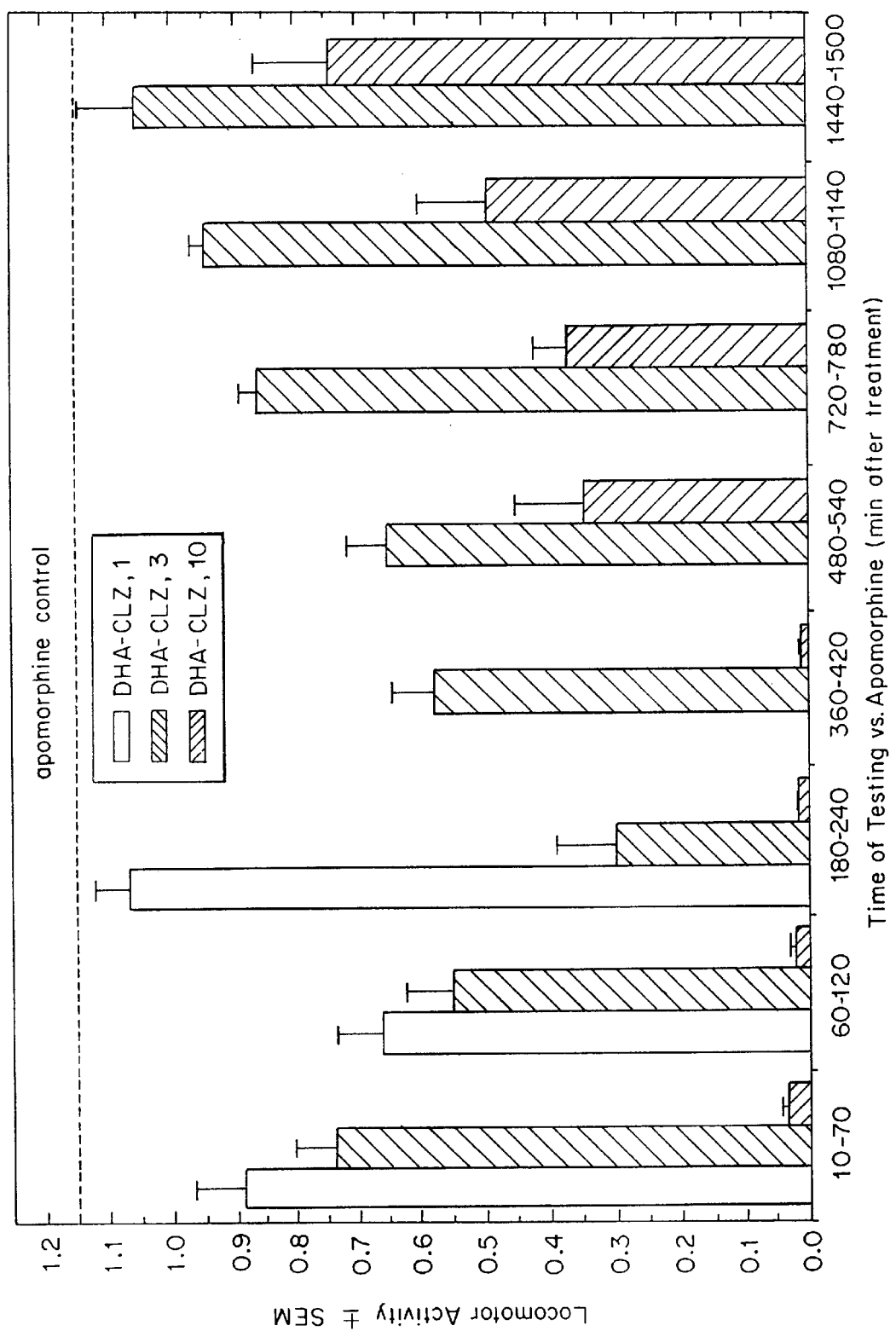
FIG. 2 is a graph which shows the dose response over time of DHA-clozapine against locomotor behavioral arousal induced by apomorphine. DHA-clozapine 1, 3, 10 refer to doses of DHA-clozapine at 1, 3 and 10 mg/kg, respectively, administered i.p.

Results:

DHA-clozapine and clozapine were both active against locomotor behavioral arousal induced by 1 mg/kg, i.p., of R(−) apomorphine, within an hour after injection of the tested central depressants at doses of 10 mg/kg, i.p. (FIGS. 1 & 2).

Figure 3:
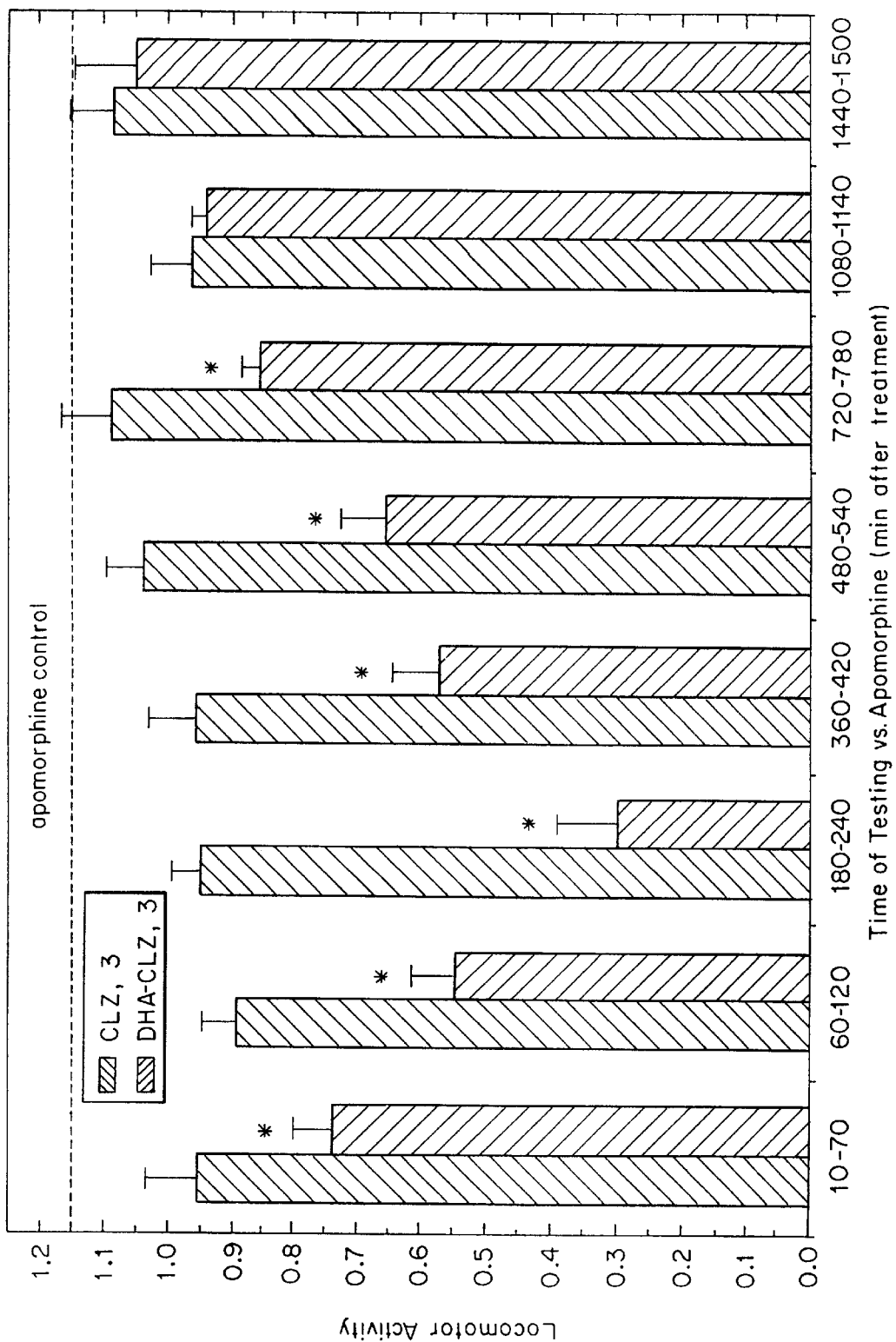
FIG. 3 is a graph which shows a comparison of the activity over time of clozapine and DHA-clozapine against locomotor behavioral arousal induced by apomorphine when administered at 3 mg/kg.

DHA-clozapine was much longer acting than clozapine, in that the effect of doses of DHA-clozapine of 3 mg/kg, i.p., persisted for 24 hours after administration. In contrast, the effect of clozapine persisted weakly for not more than 2 or 4 hours at that dose. At 10 mg/kg, DHA-clozapine produced profound inhibition of behavioral arousal that persisted for longer than 25 hours, whereas behavior had returned to control levels within 3–5 hours after administration of clozapine. Thus, DHA-clozapine was at least six-times longer-acting, and probably even more longer-acting if equimolar doses were compared. (FIGS. 2 & 3, in which asterisks indicate $p<0.05$ for planned post-hoc comparisons by Scheffé's test after a two-way ANOVA for effect of drug and testing time: F[1,80 df]=80.3 at 3 mg/kg, and F [1,80 df] 146 at 10 mg/kg; both p<0.0001 for a difference between drugs).

Figure 4:
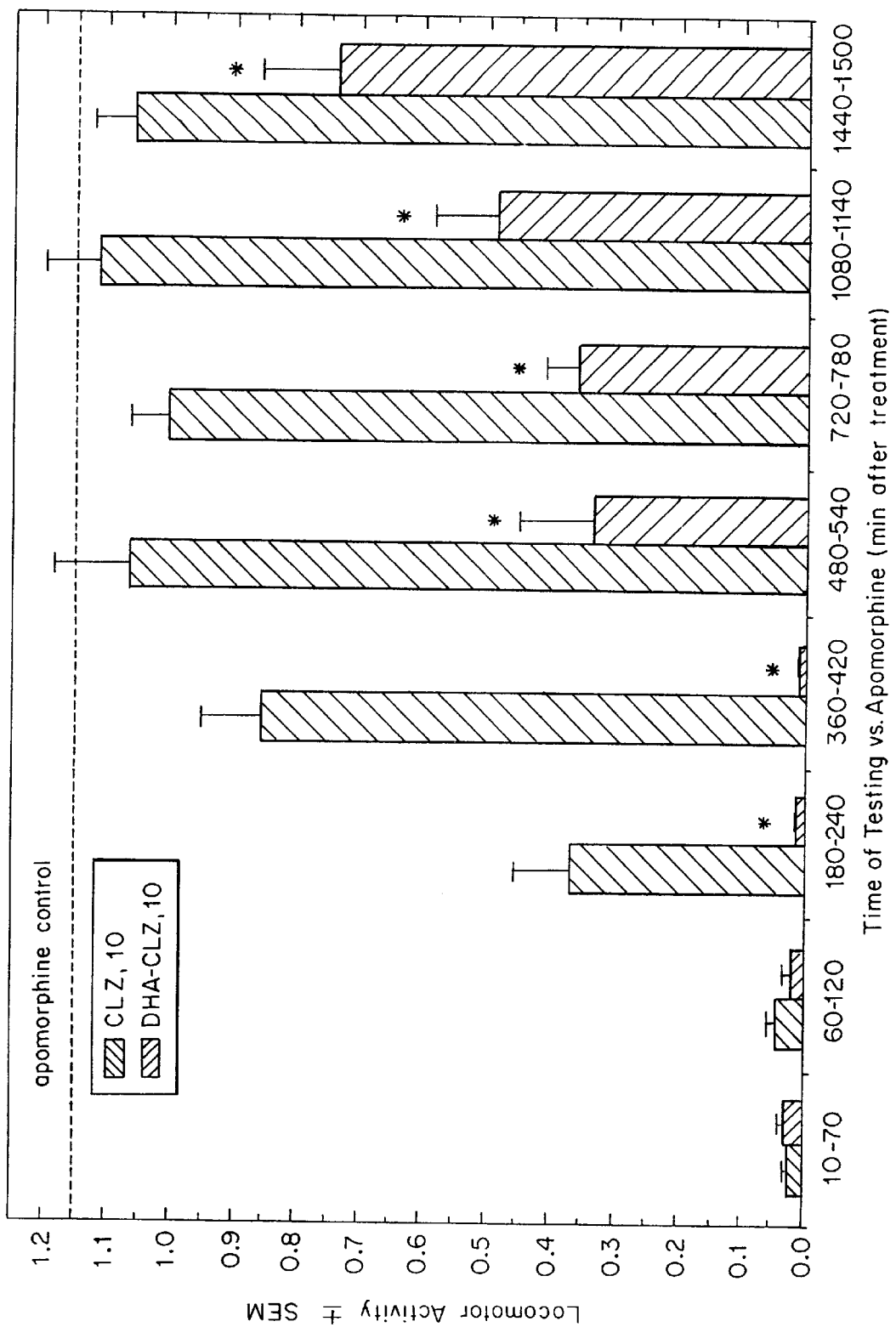
FIG. 4 is a graph which shows a comparison of the activity over time of clozapine and DHA-clozapine against locomotor behavioral arousal induced by apomorphine when administered at 10 mg/kg.
Figure 5:
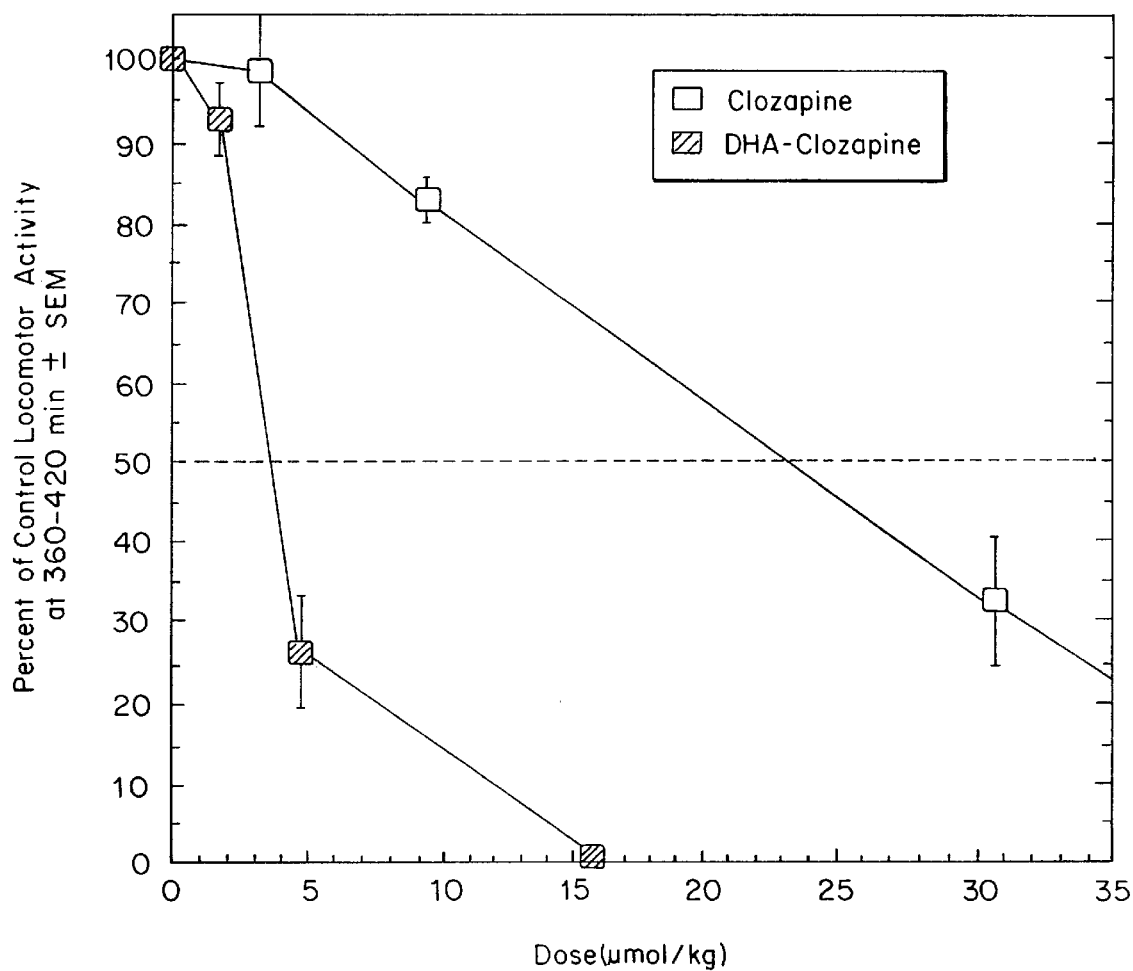
FIG. 5 is a graph which shows the molar-dose response of clozapine and DHA-clozapine at the 360–420 min time point for calculation of ED50.

On a molar-dose basis (MW of clozapine=327; DHA-clozapine=637), with testing at hours 3–4 after dosing, DHA-CLZ produced 50% inhibition of locomotor arousal induced by R(–)-apomorphine at about 3.5 μmol/kg, i.p., whereas clozapine itself required a dose of about 22.5 μmol/kg to produce the same effect (FIG. 4). Thus, the DHA-derivative was approximately 6.4-times more potent.

In conclusion, DHA-clozapine appears to be a potent, long-acting central depressant with powerful and prolonged antiapomorphine activity in the rat after systemic injection, with the ED50 of about 3.5 μmol/kg, i.p., and duration of action of more than 24 hours after doses on the order of 10–15 μmol/kg.

Such an increase in half-life has a number of medical implications such as better control of patients' psychotic symptoms since the longer half-life should allow "once a day dosing" and at lower doses. Lower total doses should result in a decrease of the peripherally and perhaps centrally mediated side-effects of clozapine.

Other aspects of the invention will be clear to the skilled artisan and need not be repeated here. All patents, published patent applications and literature cited herein are incorporated by reference in their entirety.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

We claim:

1. A composition of matter comprising
   a covalent conjugate of an antipsychotic agent and a fatty acid having 12–26 carbons except that the antipsychotic agent is not a phenothiazine, butyrophenone or thioxanthene, and wherein the antipsychotic agent is selected from the group consisting of: Alentemol Hydrobromide; Alpertine; Batelapine Maleate; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piquindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

2. The composition of matter of claim 1, wherein the fatty acid is an unbranched, naturally occurring fatty acid.

3. The composition of matter of claim 2, wherein the fatty acid has 14≧22 carbons.

4. The composition of matter of claim 2, wherein the fatty acid is docosahexaenoic acid.

5. A pharmaceutical composition comprising
   a covalent conjugate of an antipsychotic agent and a fatty acid having 12–26 carbons in an amount effective for treating a psychotic condition, and
   a pharmaceutically acceptable carrier except that the antipsychotic agent is not a phenothiazine, butyrophenone or thioxanthene, and wherein the antipsychotic agent is selected from the group consisting of: Alentemol Hydrobromide; Alpertine; Batelapine Maleate; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piquindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

6. The pharmaceutical composition of claim 5, wherein the fatty acid is an unbranched, naturally occurring fatty acid.

7. The pharmaceutical composition of claim 6, wherein the fatty acid has 14–22 carbons.

8. The pharmaceutical composition of claim 6, wherein the fatty acid is docosahexaenoic acid.

9. The pharmaceutical composition of any of claims 5–8 further comprising an antipsychotic agent other than the covalent conjugate.

10. The pharmaceutical composition of claim 9, wherein the antipsychotic agent other than the covalent conjugate is selected from the group consisting of Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate;

Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

11. A kit comprising a package housing
a container containing the covalent conjugate of any of claims 1–4, and also housing instructions for admninistering to a subject having a psychotic condition the covalent conjugate.

12. A kit comprising a package housing
a first container containing the covalent conjugate of any of claims 1–4, and
a second container containing an antipsychotic agent other that the covalent conjugate.

13. A method for treating a psychotic condition comprising
administering to a subject in need of such treatment of a covalent conjugate of an antipsychotic agent and a fatty acid having 12–26 carbons, in an amount effective to treat the psychotic condition, except that the antipychotic agent is not a phenothiazine, butyrophenone or thioxanthene, and wherein the antipsychotic agent is selected from the group consisting of Alentemol Hydrobromide; Alpertine; Batelapine Maleate; Benzindopyrine Hidrochloride; Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride, Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piguindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

14. The method of claim 13, wherein the fatty acid is an unbranched, naturally occurring fatty acid.

15. The method of claim 14, wherein the fatty acid has 14–22 carbons.

16. The method of claim 14, wherein the fatty acid is docosahexaenoic acid.

17. The method of any of claims 13–16 further comprising an antipsychotic agent other than the covalent conjugate.

18. The method of claim 17, wherein the antipsychotic agent other than the covalent conjugate is selected from the group consisting of Acetophenazine Maleate; Alentemol Hydrobrornide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Quetiapine; Remoxipride; Remoxipride Hydrochloride; Risperidone; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

19. The method of claim 13–16 wherein the psychotic condition is schizophrenia.

20. A method for achieving in a subject a therapeutic effect longer than that achieved when an equimolar amount of an antipsychotic agent is administered, comprising
administering to a subject in need of such treatment a covalent conjugate of the antipsychotic agent and a fatty acid in an amount effective to achieve said therapeutic effect, except that the antipsychotic agent is not a phenothiazine, butyrophenone or thioxanthene, and wherein the antipsychotic agent is selected from the group consisting of: Alentemol Hydrobromide; Alpertine; Batelapine Maleate; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piquindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

21. The method of claim 20, wherein the fatty acid is an unbranched, naturally occurring fatty acid.

22. The method of claim 21, wherein the fatty acid has 14–22 carbons.

23. The method of claim 21, wherein the fatty acid is docosahexaenoic acid.

24. A method for decreasing the number of daily doses required to achieve in a subject a therapeutic effect equivalent to that achieved when an equimolar amount of antipsychotic agent is administered comprising administering to a subject in need of such treatment a covalent conjugate of the antipsychotic agent and a fatty acid in an amount effective to achieve said therapeutic effect, and wherein the antipsychotic agent is selected from the group consisting of: Alentemol Hydrobromide; Alpertine; Batelapine Maleate; Benzindopyrine Hydrochloride, Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piguindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

25. The method of claim 24, wherein the fatty acid is an unbranched, naturally occurring fatty acid.

26. The method of claim 25, wherein the fatty acid has 14–22 carbons.

27. The method of claim 25, wherein the fatty acid is docosahexaenoic acid.

28. The method of claim 24–27, wherein the covalent conjugate is administered not more than once per day.

29. A method for reducing the amount of antipsychotic agent administered to a subject having a psychotic condition treatable by said antipsychotic agent, comprising administering a covalent conjugate of said antipsychotic agent and a fatty acid having 12–26 carbons to said subject at a molar dose at least 50% below the dose of the unconjugated antipsychotic agent necessary to achieve the same therapeutic effect as is achieved with said conjugate, and wherein the antipsychotic agent is selected from the group consisting of: Alentemol Hydrobromide; Alpertine; Batelapine Maleate; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Etazolate Hydrochloride; Fenimide; Flucindole; Flumezapine; Fluspirilene; Flutroline; Gevotroline Hydrochloride; Halopemide; Iloperidone; Imidoline Hydrochloride; Lenperone; Mazapertine Succinate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Pimozide; Pinoxepin Hydrochloride; Pipamperone; Piperacetazine; Pipotiazine Palmitate; Piquindone Hydrochloride; Quetiapine; Remoxipride; Quetiapine Remoxipride Hydrochloride; Risperidone; Risperadone Rimcazole Hydrochloride; Seperidol Hydrochloride; Sertindole; Setoperone; Tioperidone Hydrochloride; Tiospirone Hydrochloride; and Ziprasidone Hydrochloride.

30. The method of claim 29, wherein the fatty acid is an unbranched, naturally occurring fatty acid.

31. The method of claim 30, wherein the fatty acid has 14–22 carbons.

32. The method of claim 30, wherein the fatty acid is docosahexaenoic acid.

* * * * *